United States Patent
Wu et al.

(10) Patent No.: US 8,937,716 B2
(45) Date of Patent: Jan. 20, 2015

(54) METHOD FOR ASSESSING PERSPIRATION REDUCTION

(75) Inventors: Qiang Wu, Hillsborough, NJ (US); James Gerard Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/344,141

(22) PCT Filed: Sep. 14, 2011

(86) PCT No.: PCT/US2011/051478
§ 371 (c)(1),
(2), (4) Date: Mar. 11, 2014

(87) PCT Pub. No.: WO2013/039489
PCT Pub. Date: Mar. 21, 2013

(65) Prior Publication Data
US 2014/0340676 A1    Nov. 20, 2014

(51) Int. Cl.
*G01J 3/44*    (2006.01)
*A61B 5/00*    (2006.01)
*G01N 21/65*   (2006.01)

(52) U.S. Cl.
CPC ............. *G01N 21/65* (2013.01); *A61B 5/4266* (2013.01); *G01J 3/44* (2013.01)
USPC ......................................... 356/301; 600/306

(58) Field of Classification Search
CPC ............ G01N 21/65; G01N 2021/651; G01N 2021/653; G01N 2021/655; G01N 2021/656; G01N 21/658; G01J 3/44; A61B 5/14517; A61B 5/14521; A61B 5/4266
USPC ............................ 356/301; 600/346, 306, 307
See application file for complete search history.

(56) References Cited

U.S. PATENT DOCUMENTS

| | | | |
|---|---|---|---|
| 5,738,107 A * | 4/1998 | Martinsen et al. | 600/547 |
| 7,862,507 B2 * | 1/2011 | Crowther et al. | 600/306 |
| 8,565,850 B2 * | 10/2013 | Martinsen et al. | 600/346 |
| 2007/0049831 A1 * | 3/2007 | Crowther et al. | 600/473 |
| 2007/0083092 A1 | 4/2007 | Rippo et al. | |
| 2010/0179403 A1 * | 7/2010 | Martinsen et al. | 600/346 |
| 2011/0082352 A1 * | 4/2011 | Crowther et al. | 600/306 |

OTHER PUBLICATIONS

Boncheva et al., 2009, "Depth profiling of Stratum corneum hydration in vivo: a comparison between conductance and confocal Raman spectroscopic, measurements," Experimental Dermatol. 18(10):870-876.
Brandt et al., 2008, "Influence of climatic conditions on antiperspirant efficacy determined at different test areas," Skin Research and Technology 14(2):213-219.
Caspers et al., 2000, "Automated depth-scanning confocal Raman microspectrometer for rapid in vivo determination of water concentration profiles in human skin," J. Ramen Spectroscopy 31(8/09):813-818.
Egawa et al., 2008, "Comparison of the depth profiles of water and water-binding substances in the stratum corneum determined in vivo by Raman spectroscopy between the cheek and volar forearm skin: effects of age, seasonal changes and artificial forced hydration," British J. Dermatol. 158(2):251-260.
Egawa et al., 2009, "Changes in the depth profile of water in the stratum corneum treated with water," Skin Research Technol, 15:242-249.
FDA, 2003, "Guidelines for Effectiveness Testing of OTC Antiperspirant Drug Products", retrieved from Internet http://www.fda.gov/downloads/AboutFDA/CentersOffices/CDER/ucm106437.pdf.
International Search Report and Written Opinion in International Application No. PCT/US2011/051478, mailed Jun. 6, 2012.
Nakagawa et al., 2010, "In vivo measurement of the water content in the dermis by confocal Raman spectroscopy," Skin Research and Technology 16:137-141.
Wascotte et al., 2007, "Assessment of the "Skin Reservoir" of urea by confocal Raman microspectroscopy and reverse iontophoresis in vivo," Pharmaceutical Research 24(10):1897-1901.
Wu et al., 2008, "Confocal Raman microspectroscopy of stratum corneum: a pre-clinical validation study," International J. Cosmetic Science 30:47-56.
Wu et al., 2011, "Characterizing the composition of underarm and forearm skin using confocal raman spectrscopy," International J. Cosmetic Science 33(3):257-262.

* cited by examiner

*Primary Examiner* — Kara E Geisel
*Assistant Examiner* — Violeta A Prieto
(74) *Attorney, Agent, or Firm* — Michael F. Morgan

(57) ABSTRACT

A method to assess perspiration reduction of a composition comprising obtaining an amount of water in stratum corneum in a first area of skin on an individual using confocal Raman spectroscopy, applying a composition to the first area of skin on the individual, having the individual perform an activity to cause the individual to perspire, and obtaining an amount of water in stratum corneum in the first area of skin on the individual after the activity using confocal Raman spectroscopy.

14 Claims, No Drawings

METHOD FOR ASSESSING PERSPIRATION REDUCTION

FIELD OF THE INVENTION

The present invention relates to a method for assessing perspiration reduction of compositions

BACKGROUND OF THE INVENTION

For antiperspirant products, their efficacy can be measured using the procedure from the U.S. Food and Drug Administration, which is described in 21 CFR 350 and its subparts and in Guidelines for Effectiveness Testing of OTC Antiperspirant Drug Products (http:www.fda.gov/downloads/About-FDA/CentersOffices/CDER/ucm106437.pdf). This method describes how to apply an antiperspirant to a test subject and have the test subject sit in a hot room to measure the level of perspiration. The level of perspiration reduction is compared to an area on the test subject where no antiperspirant was applied or a control formulation was applied.

This method requires an absorbent pad to be applied to a test area to collect perspiration. The absorbent pad in the test area is compared to the control area to determine the difference in the level of perspiration between the two areas.

One drawback to this method is that the absorbent pad is in direct contact with the area where the composition is applied to the skin. While traditional antiperspirants work by penetrating the pores and forming a plug thus not remaining on the surface of skin, other compositions that can be used to reduce perspiration, such as occlusives or film formers, work by forming a layer on skin. When the absorbent pad comes into contact with the composition, the absorbent pad may remove some or all of the composition. This leads to an inaccurate result for the test. It would be desirable to have a test method that does not interfere with the test composition.

Another drawback is that the test requires a full clinical study, which is costly and time consuming. It would desirable to have a method that can be used in the laboratory to screen compositions to save time and money.

BRIEF SUMMARY OF THE INVENTION

Provided is a method to assess perspiration reduction of a composition comprising obtaining an amount of water in stratum corneum in a first area of skin on an individual using confocal Raman spectroscopy, applying a composition to the first area of skin on the individual, having the individual perform an activity to cause the individual to perspire, and obtaining an amount of water in stratum corneum in the first area of skin on the individual after the activity using confocal Raman spectroscopy.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

A method to assess perspiration reduction of a composition comprising obtaining an amount of water in stratum corneum in a first area of skin on an individual using confocal Raman spectroscopy, applying a composition to the first area of skin on the individual, having the individual perform an activity to cause the individual to perspire, and obtaining an amount of water in stratum corneum in the first area of skin on the individual after the activity using confocal Raman spectroscopy.

The method can be used to evaluate traditional antiperspirants, which are aluminum containing salts that form plugs in pores, or other materials that can reduce perspiration. Other materials that reduce perspiration can be non-aluminum materials that form plugs in pores or materials that occlude pores on the surface of skin. For materials that occlude pores on the surface of skin, these are materials that reduce the amount of perspiration by at least 5%, at least 10%, or optionally, at least 15%, at least 20%, at least 25%, at least 30%, at least 35%, at least 40%, at least 45%, at least 50%, at least 55%, at least 60%, at least 65%, at least 70%, or at least 75%. The method excludes materials that occlude pores that reduced perspiration less than 5%. Examples of such materials are traditional skin lotions. While traditional skin lotions may contain materials that can occlude skin, such as petrolatum, they are present in amounts that do not reduce perspiration greater than 5%.

The method can be used with a single application of the composition to be evaluated. Also, the method can be used with multiple applications. In multiple applications, the use of a composition over a period of time can be evaluated. The composition can be applied at least once per day and then repeated for additional days, such as 2, 3, 4, 5, 6, 7, or more days and then have the individual conduct the activity to measure the perspiration reduction. The multiple applications can show whether there is any increased effect from multiple applications.

The activity can be any activity that causes the individual to perspire. This can be the traditional hot room method (37.7° C. room at 30-40% relative humidity for 20 minutes) described in the U.S. FDA procedure listed above, or any form of exercise. Forms of exercise include peddling on a cycle, such as a stationary cycle, walking, jogging, or running, including on a treadmill, or any sporting activity. The length of the activity can be for any period of time that will generate perspiration during the activity. In certain embodiments, the amount of time is at least 5, 10, 15, 20, 30, 60 or more minutes.

The confocal Raman measurement can be any known confocal Raman method using the procedures from the manufacturer for the confocal Raman instrument. It is preferred that in a given evaluation that the same instrument and settings for measuring confocal Raman are the same for each area of skin. This will allow for a direct comparison between the different areas of skin. One method of measuring confocal Raman spectroscopy can be found in "Confocal Raman microspectroscopy of statum corneum: a pre-clinical validation study", J. Wu et al., International Journal of Cosmetic Science, 2008, 30, 47-56. In one embodiment, the confocal Raman microspectrometer is Model 3510 from River Diagnostics, Rotterdam, The Netherlands, and the settings and procedure from the manufacturer are followed.

Confocal Raman measurements will be in the stratum corneum layer of skin. A depth of skin is selected for measurement, and the total water content in the area to the depth is measured. The depth can be any desired depth. In one embodiment, the depth is up to 50 microns. In other embodiments, the depth is at least 20 or 30 microns. In one embodiment, the depth is 50 microns. Generally, the depth can be up to 20 or 30 microns. Between 30 and 50 microns, the amount of water does not generally change for skin that has a composition to be tested and skin without any composition to be tested. Because the comparison is relative, the inclusion of the amount of water between 30 to 50 microns does not change the relative difference between the areas of skin with or without a composition. The efficacy of the composition is determined by measuring the amount of water in the area of the stratum corneum up to the specified depth. Less water directly correlates to increased efficacy.

The following procedure from "Confocal Raman microspectroscopy of statum corneum: a pre-clinical validation study" can be used to determine the amount of water. The water concentration (wt %) of skin is measured to a depth of 50 μm, in 2 μm increments. The acquisition time is 1 s per step in the spectral region of 2500-4000 $cm^{-1}$. The Raman signal of skin in the 2500-4000 $cm^{-1}$ spectral region is primarily due to $-CH_2$ and $-CH_3$ stretching vibrations in protein and lipids (2800-3000 $cm^{-1}$) and to the $-H$ stretching vibrations of water (3100-3700 $cm^{-1}$). The water concentration (in mass %) is determined from the intensity ratio of two spectral intervals within these $-CH$ stretching and $-OH$ stretching regions. A $CH_3$ peak is observed at 2935 $cm^{-1}$, and an OH peak is observed at 3390 $cm^{-1}$. The area between 2910 and 2965 $cm^{-1}$ is integrated, and the area between 3350 and 3550 $cm^{-1}$ is integrated. These values are converted into the amount of water by software provided with the instrument. Any software can be used as long as the same software is used for measurements to be compared because the comparison is relative.

For the individual to be tested, typical protocols for preparing for an antiperspirant efficacy test can be followed. These include shaving the area to be tested, not using antiperspirant or other materials on the areas of skin to be tested for a period of time before applying compositions to be evaluated, such as up to 2 weeks or more, and washing the area to be tested.

In one embodiment, the method can follow the procedure from the U.S. Food and Drug Administration, which is described in 21 CFR 350 and its subparts and in Guidelines for Effectiveness Testing of OTC Antiperspirant Drug Products (http:www.fda.gov/downloads/AboutFDA/CentersOffices/CDER/ucm106437.pdf) except that instead of using the absorbent pads and collecting the perspiration, the areas of skin will be evaluated taking confocal Raman spectroscopy readings of the areas to determine the amount of water. In another embodiment, the hot room activity can be replaced by another activity, such as peddling on a stationary cycle.

The method can be used to measure the level of perspiration reduction of a composition before and after an activity. The method can also be used to compare the efficacy of different compositions with each other or against a placebo composition. An additional composition is applied to an additional area of skin (when multiple compositions are compared against skin with no composition) or to the first area of skin when a comparison is made between one or more compositions and a placebo composition. The method can also be used to compare compositions against each other without comparison to a placebo composition or an area without a composition. In this instance, one of the compositions is applied to the first area of skin.

When testing one composition or evaluating multiple compositions, the level of perspiration reduction can be calculated by subtracting the amount of water after the activity on the individual from the amount of water before the activity from the area of skin on the individual and dividing by the amount of water before the activity. When comparing one composition to another, the following formula can be used: 1−((amount of water from the first area of skin after activity/ amount of water from second area of skin after activity)/ (amount of water from the first area of skin before activity/ amount of water from second area of skin before activity)).

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. A method to assess perspiration reduction of a composition comprising:
    a) obtaining an amount of water in stratum corneum in a first area of skin on an individual using confocal Raman spectroscopy,
    b) applying a composition to the first area of skin on the individual,
    c) having the individual perform an activity to cause the individual to perspire,
    d) obtaining an amount of water in stratum corneum in the first area of skin on the individual after the activity using confocal Raman spectroscopy.

2. The method of claim 1 further comprising determining a difference in the amounts of water from the first area of skin before and after the activity comprising subtracting the amount of water after the activity on the individual from the amount of water before the activity from the first area of skin on the individual and dividing by the amount of water before the activity on the first area of skin.

3. The method of claim 1, wherein the amount of water in stratum corneum is measured at a depth of at least 15 microns.

4. The method of claim 1, wherein the skin is measured to a depth of up to 50 microns in the stratum corneum.

5. The method of claim 1, wherein the skin is measured to a depth of 20 microns in the stratum corneum.

6. The method of claim 1 further comprising applying at least one additional composition to an additional area of skin on the individual, obtaining an amount of water in the at least one additional area of skin on the individual before and after the individual performs the activity using confocal Raman spectroscopy.

7. The method of claim 6, wherein the additional composition is a placebo.

8. The method of claim 6 further comprising determining a difference in the amounts of water comprising calculating a value from 1−((amount of water from the first area of skin after activity/amount of water from second area of skin after activity)/(amount of water from the first area of skin before activity/amount of water from second area of skin before activity)).

9. The method of claim 6 further comprising determining a difference in the amounts of water from the additional area of skin before and after the activity comprising subtracting the amount of water after the activity on the individual from the amount of water before the activity from the additional area of skin on the individual and dividing by the amount of water before the activity on the additional area of skin.

10. The method of claim 1, wherein the applying comprises applying the composition to skin at least once per day for at least two days.

11. The method of claim 1, wherein the composition is an aluminum containing salt.

12. The method of claim 1, wherein the composition is not an aluminum containing salt.

13. The method of claim 1, wherein the activity is peddling on a stationary cycle, for at least 10 minutes.

14. The method of claim 1, wherein the activity is sitting in a hot room to induce perspiration.

\* \* \* \* \*